(12) United States Patent
Carney

(10) Patent No.: US 7,919,457 B2
(45) Date of Patent: Apr. 5, 2011

(54) THROMBIN PEPTIDE DERIVATIVE DIMERS

(75) Inventor: Darrell H. Carney, Dickinson, TX (US)

(73) Assignee: Orthologic Corp., Tempe, AZ (US)

( * ) Notice: Subject to any disclaimer, the term of this patent is extended or adjusted under 35 U.S.C. 154(b) by 217 days.

(21) Appl. No.: 12/287,703

(22) Filed: Oct. 10, 2008

(65) Prior Publication Data

US 2009/0124550 A1  May 14, 2009

Related U.S. Application Data

(60) Division of application No. 11/027,795, filed on Dec. 30, 2004, now Pat. No. 7,456,250, which is a continuation of application No. PCT/US03/20626, filed on Jul. 1, 2003.

(60) Provisional application No. 60/393,579, filed on Jul. 2, 2002.

(51) Int. Cl.
*C07K 14/00* (2006.01)

(52) U.S. Cl. .......................................... 514/2; 530/300

(58) Field of Classification Search ....... 514/2; 530/300
See application file for complete search history.

(56) References Cited

U.S. PATENT DOCUMENTS

| | | | |
|---|---|---|---|
| 5,500,412 A | 3/1996 | Carney et al. | |
| 6,855,687 B2 | 2/2005 | Carney et al. | |
| 6,861,407 B2 | 3/2005 | Carney | |
| 6,894,027 B2 | 5/2005 | Carney et al. | |
| 2004/0209819 A1 | 10/2004 | Carney | |
| 2005/0203017 A1 | 9/2005 | Hobson et al. | |

FOREIGN PATENT DOCUMENTS

WO  WO 98/03632 A1  1/1998

OTHER PUBLICATIONS

Norfleet, A., et al., "Thrombin Peptide TP508 Accelerates Closure of Dermal Excisions in Animal Tissue with Surgically Induced Ischemia," *Wound Repair and Regeneration*, 8(6): 517-529 (Nov.-Dec. 2000).

Norfleet, A., et al., "Thrombin Peptide, TP508, Stimulates Angiogenic Responses in Animal Models of Dermal Wound Healing, in Chick Chorioallantoic Membranes, and in Cultured Human Aortic and Microvascular Endothelial Cells," *General Pharmacology*, 35: 249-254 (Nov. 2002).

Sower, L., et al., "Thrombin Peptide, TP508, Induces Differential Gene Expression in Fibroblasts Through a Nonproteolytic Activation Pathway," *Experimental Cell Research*, 247: 422-431 (Mar. 1999).

*Primary Examiner* — Karen Cochrane Carlson
(74) *Attorney, Agent, or Firm* — Foley & Lardner LLP; Steven G. Davis

(57) ABSTRACT

Disclosed are thrombin peptide derivative dimers comprising two polypeptides having the amino acid sequence Arg-Gly-Asp-Ala-Cys-Glu-Gly-Asp-Ser-Gly-Gly-Pro-Phe-Val (SEQ ID NO:2), or a C-terminal truncated fragment of the polypeptide having at least six amino acids. Zero, one, two, or three amino acids in the polypeptide or polypeptide fragment differ from the corresponding position of SEQ ID NO:2. Also disclosed are methods of treating a subject in need of treatment with a thrombin receptor agonist. The methods comprise the step of administering an effective amount of the thrombin peptide derivative described above.

32 Claims, 2 Drawing Sheets ized. The amino acid sequence of SEQ ID NO:1 is an example of a thrombin peptide derivative.

SEQUENCE LISTING

```
<160> NUMBER OF SEQ ID NOS: 13

<210> SEQ ID NO 1
<211> LENGTH: 23
<212> TYPE: PRT
<213> ORGANISM: Artificial Sequence
<220> FEATURE:
<223> OTHER INFORMATION: C-terminal amidated fragment of human thrombin
<220> FEATURE:
<221> NAME/KEY: AMIDATION
<222> LOCATION: (23)...(23)
<223> OTHER INFORMATION: Valine is amidated as CONH2

<400> SEQUENCE: 1

Ala Gly Tyr Lys Pro Asp Glu Gly Lys Arg Gly Asp Ala Cys Glu Gly
1               5                   10                  15

Asp Ser Gly Gly Pro Phe Val
```

```
<210> SEQ ID NO 2
<211> LENGTH: 14
<212> TYPE: PRT
<213> ORGANISM: Artificial Sequence
<220> FEATURE:
<223> OTHER INFORMATION: Thrombin peptide derivative

<400> SEQUENCE: 2

Arg Gly Asp Ala Cys Glu Gly Asp Ser Gly Gly Pro Phe Val
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Thrombin peptide fragment

<400> SEQUENCE: 3

Arg Gly Asp Ala
1

<210> SEQ ID NO 4
<211> LENGTH: 14
<212> TYPE: PRT
<213> ORGANISM: Artificial Sequence
<220> FEATURE:
<223> OTHER INFORMATION: Thrombin peptide derivative
<220> FEATURE:
<221> NAME/KEY: VARIANT
<222> LOCATION: (6)...(6)
<223> OTHER INFORMATION: Xaa = Glu or Gln
<220> FEATURE:
<221> NAME/KEY: VARIANT
<222> LOCATION: (13)...(13)
<223> OTHER INFORMATION: Xaa = Phe, Met, Leu, His or Val

<400> SEQUENCE: 4

Arg Gly Asp Ala Cys Xaa Gly Asp Ser Gly Gly Pro Xaa Val
1               5                   10

<210> SEQ ID NO 5
<211> LENGTH: 23
<212> TYPE: PRT
<213> ORGANISM: Artificial Sequence
<220> FEATURE:
<223> OTHER INFORMATION: Thrombin peptide derivative

<400> SEQUENCE: 5

Ala Gly Tyr Lys Pro Asp Glu Gly Lys Arg Gly Asp Ala Cys Glu Gly
1               5                   10                  15

Asp Ser Gly Gly Pro Phe Val
            20

<210> SEQ ID NO 6
<211> LENGTH: 23
<212> TYPE: PRT
<213> ORGANISM: Artificial Sequence
<220> FEATURE:
<223> OTHER INFORMATION: Thrombin peptide derivative
<220> FEATURE:
<221> NAME/KEY: VARIANT
<222> LOCATION: (15)...(15)
<223> OTHER INFORMATION: Xaa = Glu or Gln
<220> FEATURE:
<221> NAME/KEY: VARIANT
<222> LOCATION: (22)...(22)
<223> OTHER INFORMATION: Xaa =  Phe, Met, Leu, His or Val
```

-continued

```
<400> SEQUENCE: 6

Ala Gly Tyr Lys Pro Asp Glu Gly Lys Arg Gly Asp Ala Cys Xaa Gly
1               5                   10                  15

Asp Ser Gly Gly Pro Xaa Val
            20

<210> SEQ ID NO 7
<211> LENGTH: 33
<212> TYPE: PRT
<213> ORGANISM: Artificial Sequence
<220> FEATURE:
<223> OTHER INFORMATION: Thrombin peptide derivative

<400> SEQUENCE: 7

Ala Gly Tyr Lys Pro Asp Glu Gly Lys Arg Gly Asp Ala Cys Glu Gly
1               5                   10                  15

Asp Ser Gly Gly Pro Phe Val Met Lys Ser Pro Phe Asn Asn Arg Trp
            20                  25                  30

Tyr

<210> SEQ ID NO 8
<211> LENGTH: 33
<212> TYPE: PRT
<213> ORGANISM: Artificial Sequence
<220> FEATURE:
<223> OTHER INFORMATION: Thrombin peptide derivative
<220> FEATURE:
<221> NAME/KEY: VARIANT
<222> LOCATION: (15)...(15)
<223> OTHER INFORMATION: Xaa = Glu or Gln
<220> FEATURE:
<221> NAME/KEY: VARIANT
<222> LOCATION: (22)...(22)
<223> OTHER INFORMATION: Xaa = Phe, Met, Leu, His or Val

<400> SEQUENCE: 8

Ala Gly Tyr Lys Pro Asp Glu Gly Lys Arg Gly Asp Ala Cys Xaa Gly
1               5                   10                  15

Asp Ser Gly Gly Pro Xaa Val Met Lys Ser Pro Phe Asn Asn Arg Trp
            20                  25                  30

Tyr

<210> SEQ ID NO 9
<211> LENGTH: 33
<212> TYPE: PRT
<213> ORGANISM: Artificial Sequence
<220> FEATURE:
<223> OTHER INFORMATION: Thrombin peptide derivative

<400> SEQUENCE: 9

Ala Gly Tyr Lys Pro Asp Glu Gly Lys Arg Gly Asp Ala Cys Glu Gly
1               5                   10                  15

Asp Ser Gly Gly Pro Phe Val Met Lys Ser Pro Phe Asn Asn Arg Trp
            20                  25                  30

Tyr

<210> SEQ ID NO 10
<211> LENGTH: 33
<212> TYPE: PRT
<213> ORGANISM: Artificial Sequence
<220> FEATURE:
<223> OTHER INFORMATION: Thrombin peptide derivative, C-terminal
      amidated
<220> FEATURE:
```

```
<221> NAME/KEY: AMIDATION
<222> LOCATION: (33)...(33)
<223> OTHER INFORMATION: tyrosine is amidated as CONH2

<400> SEQUENCE: 10

Ala Gly Tyr Lys Pro Asp Glu Gly Lys Arg Gly Asp Ala Cys Glu Gly
1               5                   10                  15

Asp Ser Gly Gly Pro Phe Val Met Lys Ser Pro Phe Asn Asn Arg Trp
            20                  25                  30

Tyr

<210> SEQ ID NO 11
<211> LENGTH: 23
<212> TYPE: PRT
<213> ORGANISM: Artificial Sequence
<220> FEATURE:
<223> OTHER INFORMATION: Thrombin peptide derivative
<220> FEATURE:
<221> NAME/KEY: VARIANT
<222> LOCATION: (15)...(15)
<223> OTHER INFORMATION: Xaa = Glu or Gln
<220> FEATURE:
<221> NAME/KEY: VARIANT
<222> LOCATION: (22)...(22)
<223> OTHER INFORMATION: Xaa = Phe, Met, Leu, His or Val
<220> FEATURE:
<221> NAME/KEY: AMIDATION
<222> LOCATION: (23)...(23)
<223> OTHER INFORMATION: Valine is amidated as CONH2

<400> SEQUENCE: 11

Ala Gly Tyr Lys Pro Asp Glu Gly Lys Arg Gly Asp Ala Cys Xaa Gly
1               5                   10                  15

Asp Ser Gly Gly Pro Xaa Val
            20

<210> SEQ ID NO 12
<211> LENGTH: 12
<212> TYPE: PRT
<213> ORGANISM: Artificial Sequence
<220> FEATURE:
<223> OTHER INFORMATION: Thrombin peptide derivative

<400> SEQUENCE: 12

Asp Ala Cys Glu Gly Asp Ser Gly Gly Pro Phe Val
1               5                   10

<210> SEQ ID NO 13
<211> LENGTH: 4
<212> TYPE: PRT
<213> ORGANISM: Artificial Sequence
<220> FEATURE:
<223> OTHER INFORMATION: Fibronectin fragment

<400> SEQUENCE: 13

Arg Gly Ala Ser
1
```

THROMBIN PEPTIDE DERIVATIVE DIMERS

RELATED APPLICATION(S)

This application is a divisional of U.S. application Ser. No. 11/027,795, filed Dec. 30, 2004, now U.S. Pat. No. 7,456,250, which is a continuation of International Application No. PCT/US2003/020626, which designated the United States and was filed Jul. 1, 2003, published in English, which claims the benefit of U.S. Provisional Application No. 60/393,579, filed Jul. 2, 2002. The entire teachings of the above applications are incorporated herein by reference.

BACKGROUND OF THE INVENTION

Thrombin, a multi-functional enzyme already known for its blood-clotting activity, has been recently reported to be an important cell-growth factor. For example, thrombin has been shown to promote angiogenesis, the development of new blood vessels, and to stimulate endothelial cell proliferation. These processes are a pivotal part of healing wounds.

Thrombin peptide derivatives are molecules having an amino acid sequence derived at least in part from that of thrombin, which are active at certain thrombin receptors. For example, thrombin peptide derivatives from amino acids 508-530 of human pro-thrombin have been described by the present inventors for promoting thrombin receptor mediated cell stimulation and for their use in the treatment of wounds, and stimulation of angiogenesis (see, e.g., U.S. Pat. No. 5,500,412 or No. 5,352,664, the contents of which are incorporated herein by reference in their entirety). Because of their biological activity, these thrombin peptide derivatives show great potential as pharmaceuticals. TP508 is one such example of a thrombin peptide derivative and has the amino acid sequence of H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO:1).

Strict regulations by the Food and Drug Administration (FDA) require a high degree of purity of biologically active agents when used as pharmaceuticals. It therefore is necessary to obtain active thrombin peptide derivatives that maintain their purity over extended time periods, if these compounds are to be used to treat humans. For example, the purity of TP508 diminishes over time because of dimerization. For example, TP508 has a half-life of about 2 to about 4 hours in buffered solutions at neutral pH.

SUMMARY OF THE INVENTION

It has now been found that thrombin peptide derivative dimers retain activity toward thrombin receptors. Thrombin peptide derivative dimers can be prepared essentially free of monomer and have about the same level of activity toward the thrombin receptor as TP508 (see Example 3). The thrombin peptide derivative dimers also retain their purity with minimal reversion to monomer (see Example 2). Based on this discovery, the invention provides novel peptide dimers, pharmaceutical compositions comprising these peptide dimers, and methods useful for treating a subject in need of treatment with a thrombin receptor agonist.

One embodiment of the present invention is a thrombin peptide derivative dimer comprising two thrombin peptide derivatives. Each thrombin peptide derivative independently comprises a polypeptide which has the amino acid sequence Arg-Gly-Asp-Ala-Cys-Glu-Gly-Asp-Ser-Gly-Gly-Pro-Phe-Val (SEQ ID NO:2), or a C-terminal truncated fragment thereof having at least six amino acids. Zero, one, two, or three amino acids in the polypeptide differ from the corresponding position of SEQ ID NO:2. Preferably the difference is conservative. The thrombin peptide derivatives are optionally amidated at the C-terminus and/or acylated at the N-terminus.

Another embodiment of the invention also relates to pharmaceutical compositions comprising a thrombin receptor agonist or a thrombin peptide derivative dimer described herein and a pharmaceutically acceptable carrier or diluent.

Another embodiment of the invention further relates to methods of treating a subject in need of treatment with a thrombin receptor agonist. The methods comprise the step of administering an effective amount of a thrombin peptide derivative dimer described herein.

Advantages of the thrombin peptide derivative dimers of the present invention include longer storage life in solution compared with the monomer TP508. Therefore, it is possible to deliver precise and reproducible dosages with the disclosed peptides, even after storage for prolonged periods of time. The thrombin peptide derivative dimers described herein are also inexpensive to produce. The thrombin peptide derivative dimers can be used in the treatment and/or prevention of diseases and/or conditions in which angiogenesis and cell proliferation would be beneficial. The thrombin peptide derivative dimers can be used to help treat, for example, wounds such as diabetic ulcers, bone fractures, and cartilage damage. The thrombin peptide derivative dimers can also be used to prevent restenosis in patients after angioplasty and regenerate blood vessels in cardiac tissue.

DETAILED DESCRIPTION OF THE INVENTION

Figure 1:
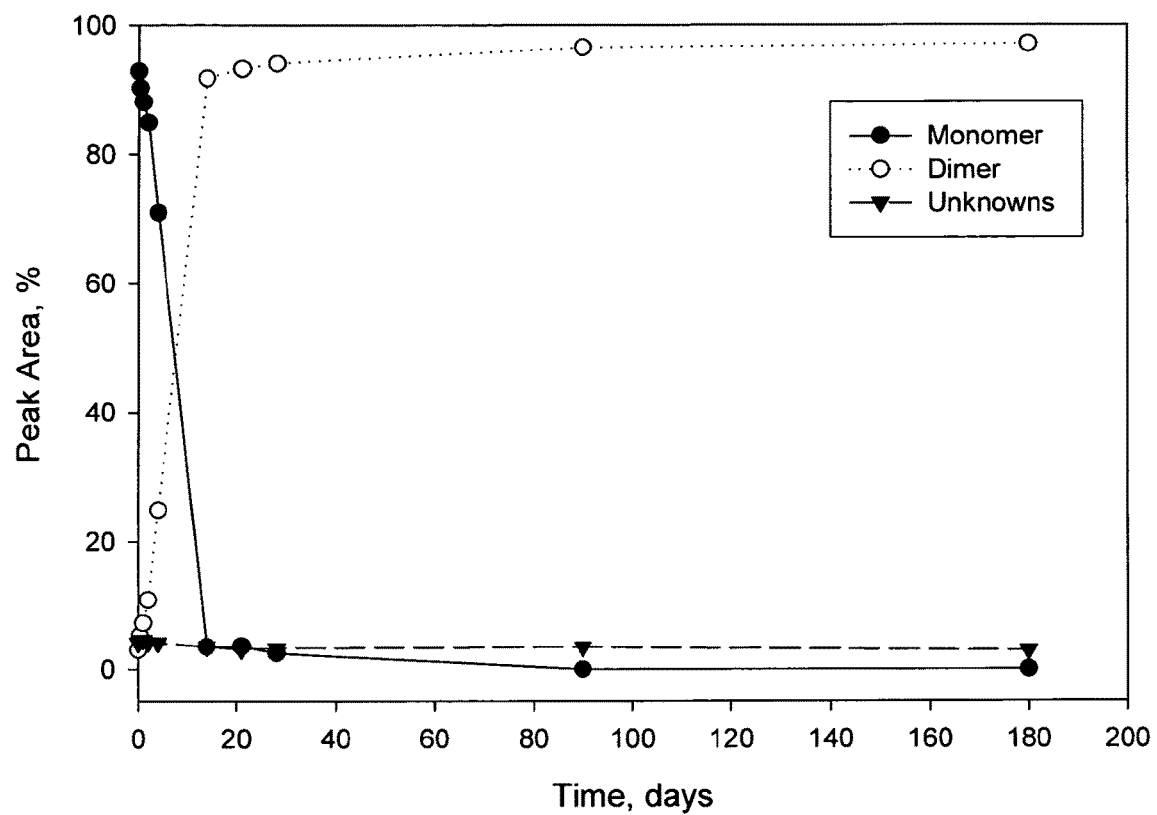
FIG. 1 is a graph showing the conversion of TP508 to dimer over time. The graph shows the HPLC peak area measurements of TP508-monomer, TP508-dimer and unknowns found in samples of TP508 saline solution (5 mg/mL, incubated at 4° C.), taken at intervals over a time period of 6 months. Peak area is indicated as percent. Time is indicated as days. Monomer is indicated as (—●—). Dimer is indicated as (—○—). Unknowns are indicated as (—▼—).

Applicants have found that the thrombin peptide derivative dimers of the present invention essentially do not revert to monomers and still have about the same biological activity as the thrombin peptide derivatives of the prior art. A "thrombin peptide derivative dimer" is a molecule comprising two thrombin peptide derivatives linked by a covalent bond, preferably a disulfide bond between cysteine residues. Thrombin peptide derivative dimers are typically essentially free of the corresponding monomer, e.g., greater than 95% free by weight and preferably greater than 99% free by weight. Preferably the polypeptides are the same and covalently linked through a disulfide bond.

It will be understood that the thrombin peptide derivatives disclosed herein can have C-terminal amides. A "C-terminal amide" is an amide at the C-terminal amino acid residue in which the alpha carboxylic acid is replaced with an amide. For example, C-terminal amino acid amide residues have the formula: —NH—CH($R_a$)—C(O)—$NR_bR_c$. $R_a$ is an amino acid side chain. An amino acid side chain can be hydrogen, a substituted or unsubstituted $C_1$-$C_{10}$ aliphatic group, or a substituted or unsubstituted $C_1$-$C_{10}$ aromatic group. Preferably Ra is an amino acid side chain corresponding to naturally occurring amino acids. $R_b$ and $R_c$ are independently hydrogen, a $C_1$-$C_{10}$ substituted or unsubstituted aliphatic group, or $R_b$ and $R_c$, taken together with the nitrogen to which they are bonded, form a $C_1$-$C_{10}$ non-aromatic heterocyclic group. Preferably, the C-terminal amide is —C(O)$NH_2$ (carboxamide). As used herein, "—$NH_2$" at the C-terminus indicates a C-terminus carboxamide; "—OH" at the C-terminus indicates that the peptide has a free C-terminus; and no designation at the C-terminus indicates that the peptide is amidated at the C-terminus or has a free C-terminus.

It will also be understood that the thrombin peptide derivatives disclosed herein can have an acylated N-terminus. An "acylated N-terminus" is an N-terminal amino acid residue in which the nitrogen of the N-terminal amino acid residue is acylated. For example, acylated N-terminal amino acids residues have the formula: $R_d$C(O)—NH—$CHR_a$—C(O)—. $R_d$ is hydrogen, a $C_1$-$C_{10}$ substituted or unsubstituted aliphatic group, or a $C_1$-$C_{10}$ substituted or unsubstituted aromatic group. Acetyl is a preferred acyl group. An "—H" at the N-terminus indicates that the N-terminus is unsubstituted; and no designation at the N-terminus indicates that the terminus is acylated or unsubstituted.

Preferably, the N-terminus of a thrombin peptide derivative is free (i.e., unsubstituted) and the C-terminus is free (i.e., unsubstituted) or amidated, preferably a carboxamide (i.e., —C(O)$NH_2$).

Thrombin peptide derivatives are believed to activate cells by binding to a high-affinity cell-surface thrombin receptor known as the non-proteolytically-activated thrombin receptor (hereinafter "NPAR") (R. Horvat, et. al., *J. Cell Sci.* 108, 1155-1164, 1995). Compounds which stimulate NPAR are said to be thrombin receptor agonists. NPAR activation can be assayed based on the ability of molecules to stimulate cell proliferation when added to fibroblasts in the presence of submitogenic concentrations of thrombin or molecules that activate protein kinase C or compete with $^{125}$I-thrombin for high affinity binding to thrombin receptors, as disclosed in U.S. Pat. Nos. 5,352,664 and 5,500,412 and in Glenn et al., *J. Peptide Research* 1:65 (1988).

To further identify regions of thrombin involved in high-affinity binding and generation of mitogenic signals, two peptides representing specific domains within p508-530 were tested. The first peptide represented residues 519 to 530 of the B-chain region of human prothrombin, a region of thrombin that is highly conserved among serine proteases. The second peptide represented residues 517 to 520 of prothrombin, a region of thrombin homologous to the fibronectin cell binding domain.

Both of these peptides were able to compete for 30% to 50% of the binding of $^{125}$I-alpha-thrombin to ME cells, but both required higher concentrations than was required with the initial peptide p508-530 (Table 1). For example, 30% inhibition of $^{125}$I-alpha-thrombin binding required 33- to 50-fold higher concentrations of p519-530 and p517-520 than p508-530, respectively. Thus, both of these peptides appear to interact with thrombin receptors, but at a lower affinity than p508-530. Because p517-520 is homologous to the fibronectin cell binding domain, a peptide having the sequence Arg-Gly-Ala-Ser (SEQ ID NO:13; the sequence of the fibronectin specific peptide) was also tested for its ability to compete for $^{125}$I-alpha-thrombin binding. At a concentration of 1.3 µM, this peptide did not compete with $^{125}$I-alpha-thrombin for binding. Thus, the receptor for alpha-thrombin is not the same membrane protein that specifically interacts with fibronectin and causes the apparent growth promoting action of fibronectin. In addition, these results demonstrate the requirement for alanine within the thrombin receptor binding domain, since substitution of alanine with serine eliminated the ability of the synthetic peptide to compete for alpha-thrombin binding.

TABLE

Comparison of Peptide Competition for [125]I-Alpha-Thrombin Binding to ME Cells.

| Peptide | Amino Acid Sequence | Concentration Required for 30% Inhibition | Maximal % Inhibition (and Conc.) |
| --- | --- | --- | --- |
| p508-530 | AGYKPDEG-KRGDACE-GDSGGPFV (SEQ ID NO: 5) | 6 nM | 78% (40 nM) |
| p519-530 | DACEGDSGGPFV (SEQ ID NO: 12) | 200 nM | 51% (800 nM) |
| p517-520 | RGDA (SEQ ID NO: 3) | 300 nM | 50% (2.7 µM) |

The mitogenic activity of the smaller thrombin derivatives, p519-530 and p517-520, was tested. As indicated above, both of these peptides bind to the high-affinity thrombin receptor. In these experiments, increasing concentrations of p519-530 and p517-520 were added to quiescent NIL cells in the presence of 2 and 4 nM alpha-thrombin. As shown in FIG. 6 of U.S. Pat. No. 5,500,412, p519 enhanced DNA synthesis over a range of concentrations while p517-520 did not. In fact, p517-520 actually inhibited DNA synthesis.

Thrombin peptide derivatives stimulate NPAR and have less than about fifty amino acids, preferably less than about thirty-three amino acids. Thrombin peptide derivatives also have sufficient homology to the fragment of human thrombin corresponding to prothrombin amino acids 508-530: Ala-Gly-Tyr-Lys-Pro-Asp-Glu -Gly-Lys-Arg-Gly-Asp-Ala-Cys-Glu-Gly-Asp-Ser-Gly-Gly-Pro-Phe-Val (SEQ ID NO:5) so that the polypeptide activates NPAR. The thrombin peptide derivative dimers described herein are formed from polypeptides typically having at least six amino acids and preferably between about 12 and 33 amino acids, more preferably between about 12 and 23 amino acids.

In a first preferred embodiment, each thrombin peptide derivative comprises a polypeptide having the amino acid sequence Arg-Gly-Asp-Ala-Cys-$X_1$-Gly-Asp-Ser -Gly-Gly-Pro-$X_2$-Val (SEQ ID NO:4), or a C-terminal truncated fragment thereof having at least six amino acids. More preferably, each thrombin peptide derivative has the amino acid sequence Ala-Gly-Tyr-Lys-Pro-Asp-Glu-Gly-Lys-Arg-Gly-Asp-Ala-Cys -Glu-Gly-Asp-Ser-Gly-Gly-Pro-Phe-Val (SEQ ID NO:5), or a fragment thereof comprising amino acids 10-18 of SEQ ID NO:5. Even more preferably, the thrombin peptide derivative has the amino acid sequence Ala-Gly-Tyr-Lys-Pro-Asp-Glu-Gly -Lys-Arg-Gly-Asp-Ala-Cys-$X_1$-Gly-Asp-Ser-Gly-Gly-Pro-$X_2$-Val (SEQ ID NO:6), or a fragment thereof comprising amino acids 10-18 of SEQ ID NO:6. $X_1$ is Glu or Gln and $X_2$ is Phe, Met, Leu, His or Val. Preferably $X_1$ is Glu, and $X_2$ is Phe. One example of a thrombin peptide derivative of this type is a polypeptide having the amino acid sequence Ala-Gly-Tyr-Lys-Pro-Asp-Glu-Gly-Lys-Arg-Gly-Asp-Ala-Cys-Glu-Gly-Asp -Ser-Gly-Gly-Pro-Phe-Val (SEQ ID NO:5). A further example of a thrombin peptide derivative of this type is a polypeptide having the amino acid sequence H-Ala-Gly-Tyr -Lys-Pro-Asp-Glu-Gly-Lys-Arg-Gly-Asp-Ala-Cys-Glu-Gly-Asp-Ser-Gly-Gly-Pro-Phe -Val-NH$_2$ (SEQ ID NO: 1). Zero, one, two or three amino acids in the thrombin peptide derivative differ from the amino acid at the corresponding position of SEQ ID NO:1, 4, 5 or 6. Preferably, the difference is conservative.

One example of a thrombin peptide derivative dimer of the present invention is represented by Formula I:

polypeptide with another amino acid from the same group results in a conservative substitution:

Group I: glycine, alanine, valine, leucine, isoleucine, serine, threonine, cysteine, and non-naturally occurring amino acids with C1-C4 aliphatic or C1-C4 hydroxyl substituted aliphatic side chains (straight chained or monobranched).

Group II: glutamic acid, aspartic acid and non-naturally occurring amino acids with carboxylic acid substituted C1-C4 aliphatic side chains (unbranched or one branch point).

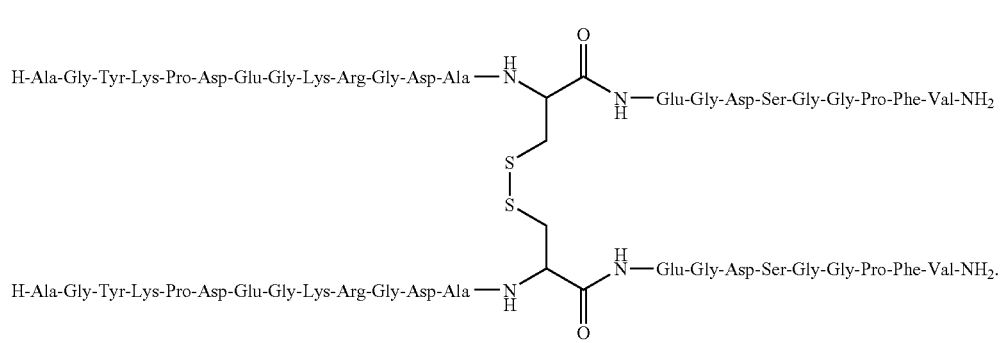

(I)

In a second preferred embodiment, each thrombin peptide derivative comprises a polypeptide having the amino acid sequence Ala-Gly-Tyr-Lys-Pro-Asp-Glu-Gly-Lys -Arg-Gly-Asp-Ala-Cys-Glu-Gly-Asp-Ser-Gly-Gly-Pro-Phe-Val-Met-Lys-Ser-Pro-Phe -Asn-Asn-Arg-Trp-Tyr (SEQ ID NO:7), or a C-terminal truncated fragment thereof having at least twenty-three amino acids. More preferably, each thrombin peptide derivative has the amino acid sequence Ala-Gly-Tyr-Lys-Pro-Asp-Glu-Gly-Lys-Arg -Gly-Asp-Ala-Cys-X$_1$-Gly-Asp-Ser-Gly-Gly-Pro-X$_2$-Val-Met-Lys-Ser-Pro-Phe-Asn -Asn-Arg-Trp-Tyr (SEQ ID NO:8), or a C-terminal truncated fragment thereof having at least twenty-three amino acids. X$_1$ is Glu or Gln and X$_2$ is Phe, Met, Leu, His or Val. Preferably X$_1$ is Glu, and X$_2$ is Phe. One example of a thrombin peptide derivative of this type is a polypeptide having the amino acid sequence Ala-Gly-Tyr-Lys-Pro-Asp -Gly-Gly-Lys-Arg-Gly-Asp-Ala-Cys-Glu-Gly-Asp-Ser-Gly-Gly-Pro-Phe-Val-Met-Lys -Ser-Pro-Phe-Asn-Asn-Arg-Trp-Tyr (SEQ ID NO:9). A further example of a thrombin peptide derivative of this type is a polypeptide having the amino acid sequence H-Ala -Gly-Tyr-Lys-Pro-Asp-Glu-Gly-Lys-Arg-Gly-Asp-Ala-Cys-Glu-Gly-Asp-Ser-Gly-Gly -Pro-Phe-Val-Met-Lys-Ser-Pro-Phe-Asn-Asn-Arg-Trp-Tyr-NH$_2$ (SEQ ID NO:10). Zero, one, two or three amino acids in the thrombin peptide derivative differ from the amino acid at the corresponding position of SEQ ID NO:7, 8, 9 or 10. Preferably, the difference is conservative.

A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in the their side chains differs by no more than one. Amino acids with phenyl or substituted phenyl groups in their side chains are considered to have about the same size and shape. Listed below are five groups of amino acids. Replacing an amino acid in a Group III: lysine, ornithine, arginine and non-naturally occurring amino acids with amine or guanidino substituted C1-C4 aliphatic side chains (unbranched or one branch point).

Group IV: glutamine, asparagine and non-naturally occurring amino acids with amide substituted C1-C4 aliphatic side chains (unbranched or one branch point).

Group V: phenylalanine, phenylglycine, tyrosine and tryptophan.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in the their side chains. Examples of highly conservative substitutions include valine for leucine, threonine for serine, aspartic acid for glutamic acid and phenylglycine for phenylalanine. Examples of substitutions which are not highly conservative include alanine for valine, alanine for serine and aspartic acid for serine.

An "N-terminal truncated fragment" refers to a fragment remaining after removing an amino acid or block of amino acids from the N-terminus, preferably a block of no more than six amino acids, more preferably a block of no more than three amino acids. Optionally, an N-terminal truncated fragment is acylated and/or amidated as described above.

A "C-terminal truncated fragment" refers to a fragment remaining after removing an amino acid or block of amino acids from the C-terminus, preferably a block of no more than six amino acids, more preferably a block of no more than three amino acids. Optionally, a C-terminal truncated fragment is amidated and/or acylated as described above.

A "non-aromatic heterocyclic group," as used herein, is a non-aromatic carbocyclic ring system that has 3 to 10 atoms and includes at least one heteroatom, such as nitrogen, oxygen, or sulfur. Examples of non-aromatic heterocyclic groups include piperazinyl, piperidinyl, pyrrolidinyl, morpholinyl and thiomorpholinyl.

The term "aryl group," as used herein, includes both carbocyclic and heterocyclic aromatic ring systems. Examples of aryl groups include phenyl, indolyl, furanyl and imidazolyl.

An "aliphatic group" is a straight chain, branched or cyclic non-aromatic hydrocarbon. An aliphatic group can be completely saturated or contain one or more units of unsaturation (e.g., double and/or triple bonds), but is preferably saturated, i.e., an alkyl group. Typically, a straight chained or branched aliphatic group has from 1 to about 10 carbon atoms, preferably from 1 to about 4, and a cyclic aliphatic group has from 3 to about 10 carbon atoms, preferably from 3 to about 8. Aliphatic groups include, for example, methyl, ethyl, n-propyl, iso-propyl, n-butyl, sec-butyl, tert-butyl, pentyl, cyclopentyl, hexyl, cyclohexyl, octyl and cyclooctyl.

Suitable substituents for an aliphatic group, an aryl group or a non-aromatic heterocyclic group are those which do not significantly lower therapeutic activity of the thrombin peptide derivative, for example, those found on naturally occurring amino acids. Examples include —OH, a halogen (—Br, —Cl, —I and —F), —O($R_e$), —O—CO—($R_e$), —CN, —$NO_2$, —COOH, =, —$NH_2$—NH($R_e$), —N($R_e$)$_2$, —COO($R_e$), —$CONH_2$, —CONH($R_e$), —CON($R_e$)$_2$—SH, —S($R_e$), an aliphatic group, an aryl group and a non-aromatic heterocyclic group. Each $R_e$ is independently an alkyl group or an aryl group. A substituted aliphatic group can have more than one substituent.

A "subject" is preferably a human, but can also be an animal in need of treatment with a thrombin receptor agonist, e.g., companion animals (e.g., dogs, cats, and the like), farm animals (e.g., cows, pigs, horses and the like) and laboratory animals (e.g., rats, mice, guinea pigs and the like).

Subjects "in need of treatment" with a thrombin receptor agonist, are subjects with diseases and/or conditions that can be treated with thrombin receptor agonists and thrombin peptide derivative dimers to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment requires cell proliferation involving chondrocytes, angiogenesis, bone growth, cardiac repair, wound healing or inhibition of restenosis.

Thrombin peptide derivatives have been shown to stimulate proliferation of endothelial cells, fibroblasts, and keratinocytes (see, e.g., U.S. Pat. No. 5,500,412 or No. 5,352,664, the contents of which are incorporated herein by reference in their entirety). The disclosed thrombin peptide derivative dimers can therefore be used to promote healing in acute wounds such as burns, dermal wounds, surgical wounds, and bone fractures. In addition, thrombin peptide derivatives have recently been shown to be particularly effective in promoting the healing of chronic wounds such as, diabetic ulcers, venous ulcers, and pressure sores (see, e.g., WO 03/013569, the contents of which are incorporated herein by reference in their entirety). Thrombin peptide derivatives have also been shown to stimulate the growth of chondrocytes (see, e.g., WO 02/07748, the contents of which are incorporated herein by reference in their entirety). Thus thrombin peptide derivatives, including the compounds of the present invention can be used to stimulate chondrocyte growth and repair in, for example patients with osteoarthritis or joint injuries. Other uses for thrombin peptide derivatives, including those of the present invention, include stimulating bone growth to promote healing of simple fractures, non-union fractures, voids and gaps in bone and bone grafts, preventing restenosis in patients after angioplasty and promoting the regeneration of blood vessels in cardiac tissue (see, e.g., WO 02/005836 and WO 02/004008, the contents of which are incorporated herein by reference in their entirety).

An "effective amount" is the quantity of thrombin peptide derivative dimer that results in an improved clinical outcome of the condition being treated with the thrombin peptide derivative dimer compared with the absence of treatment. The amount of thrombin peptide derivative dimer administered will depend on the degree, severity, and type of the disease or condition, the amount of therapy desired, and the release characteristics of the pharmaceutical formulation. It will also depend on the subject's health, size, weight, age, sex and tolerance to drugs. Typically, the agonist is administered for a sufficient period of time to achieve the desired therapeutic effect. Typically between about 1 µg per day and about 1 mg per day of the thrombin peptide derivative (preferably between about 5 µg per day and about 100 µg per day) is administered to the subject in need of treatment.

The thrombin peptide derivative dimer can be administered by any suitable route, locally or systemically, including, for example, by parenteral administration. Parenteral administration can include, for example, intramuscular, intravenous, subcutaneous, or intraperitoneal injection. Topical administration for treating wounds can include, for example, creams, gels, ointments or aerosols. Respiratory administration can include, for example, inhalation or intranasal drops. For certain indications such as stimulating bone growth, cartilage repair, cardiac repair and the treatment of restenosis, it is advantageous to inject or implant the thrombin peptide derivative directly to the treatment site. The thrombin peptide derivative dimer can also be advantageously administered in a sustained release formulation.

The thrombin peptide derivative dimer can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers should be biocompatible, i.e., non-toxic, non-inflammatory, non-immunogenic and devoid of other undesired reactions at the administration site. Examples of pharmaceutically acceptable carriers include, for example, saline, aerosols, commercially available inert gels, or liquids supplemented with albumin, methyl cellulose or a collagen matrix. Standard pharmaceutical formulation techniques can be employed, such as those described in Remington's Pharmaceutical Sciences, Mack Publishing Company, Easton, Pa.

For indications such as bone growth, cartilage repair, cardiac repair and inhibition of restenosis, it may be advantageous to administer the thrombin peptide derivative in a sustained release formulation. Polymers are often used to form sustained release formulations. Examples of these polymers include poly α-hydroxy esters such as polylactic acid/polyglycolic acid homopolymers and copolymers, polyphosphazenes (PPHOS), polyanhydrides and poly(propylene fumarates).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson, et al., *Adv. Drug Deliv. Rev.* 28.5 (1997), the entire teachings of which are incorporated herein by reference). The incorporation of poly(ethylene glycol) into the polymer as a blend to form microparticle carriers allows further alteration of the release profile of the active ingredient (see Cleek et al., *J. Control Release* 48.259 (1997), the entire teachings of which are incorporated herein by reference). Ceramics such as calcium phosphate and hydroxyapatite can also be incorporated into the formulation to improve mechanical qualities.

PPHOS polymers contain alternating nitrogen and phosphorous with no carbon in the polymer backbone, as shown below in Structural Formula (II):

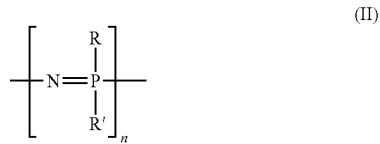

The properties of the polymer can be adjusted by suitable variation of side groups R and R' that are bonded to the polymer backbone. For example, the degradation of and drug release by PPHOS can be controlled by varying the amount of hydrolytically unstable side groups. With greater incorporation of either imidazolyl or ethylglycol substituted PPHOS, for example, an increase in degradation rate is observed (see Laurencin et al., *J. Biomed Mater. Res.* 27:963 (1993), the entire teachings of which are incorporated herein by reference), thereby increasing the rate of drug release.

Polyanhydrides, shown in Structural Formula (III), have well defined degradation and release characteristics that can be controlled by including varying amounts of hydrophobic or hydrophilic monomers such as sebacic acid and 1,3-bis(p-carboxyphenoxy)propane (see Leong et al., *J. Biomed. Mater. Res.* 19:941 (1985), the entire teachings of which are incorporated herein by reference). To improve mechanical strength, anhydrides are often copolymerized with imides to form polyanhydride-co-imides. Examples of polyanhydride-co-imides that are suitable for orthopaedic applications are poly(trimellitylimido-glycine-co-1,6-bis(carboxyphenoxy) hexane and pyromellityimidoalanine: 1,6-bis(p-carboxyphenoxy)hexane copolymers.

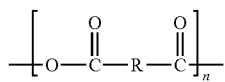

Carriers for stimulating bone or cartilage growth advantageously include porous matrices which can then serve as a scaffolding for bone and tissue growth onto which bone progenitor cells and osteogenic cells may migrate and attach. Such carriers are said to be osteoconductive. For certain applications, the carrier should have sufficient mechanical strength to maintain its three dimensional structure and help support the immobilization of the bone or tissue segments being united or grafted together.

Examples of suitable osteoconductive carriers include collagen (e.g., bovine collagen), fibrin, calcium phosphate ceramics (e.g., hydroxyapatite and tricalcium phosphate), calcium sulfate, guanidine-extracted allogenic bone and combinations thereof. A number of suitable carriers are commercially available, such as COLLAGRAFT® (Cohension Technologies, Inc., Palo Alto, Calif.), which is a mixture of hydroxyapatite, tricalcium phosphate and fibrillar collagen, and PRO OSTEON 500™ (Interpore Cross International, Irvine, Calif.), which is a hydroxyapatite biomatrix formed by the conversion of marine coral calcium carbonate to crystalline hydroxyapatite.

Descriptions of synthetic biodegradable polymers that can serve as osteoconductive carriers with sustained release characteristics, can be found in Behravesh et al., *Clinical Orthopaedics* 367:S118 (1999) and Lichun et al., *Polymeric Delivery Vehicles for Bone Growth Factors* in "Controlled Drug Delivery—Designing Technologies for the Future" Park and Mrsny eds., American Chemical Society, Washington, D.C. (2000). The entire teachings of these references are incorporated herein by reference. Examples of these polymers include poly α-hydroxy esters such as polylactic acid/polyglycolic acid homopolymers and copolymers, polyphosphazenes (PPHOS), polyanhydrides and poly(propylene fumarates), which are described above in detail.

Implantable pharmaceutical compositions of the present invention are particularly useful because they can be administered at a site in need of bone growth. "Implantation" or "administration at a site" means in sufficient proximity to the site in need of treatment so that bone growth occurs (e.g., more bone growth in the presence of the drug than in its absence) at the site when the thrombin peptide derivative dimer is released from the pharmaceutical composition. These pharmaceutical compositions can be shaped as desired in anticipation of surgery or shaped by the physician or technician during surgery. It is preferred to shape the matrix to span a tissue defect and to take the desired form of the new tissue. In the case of bone repair of a non-union defect, for example, it is desirable to use dimensions that span the non-union. In bone formation procedures, the material is slowly absorbed by the body and is replaced by bone in the shape of or very nearly the shape of the implant. Alternatively, the pharmaceutical compositions can be administered to the site in the form of microparticles or microspheres. The microparticles are placed in contact or in close proximity to the site in need of osteoconduction either by surgically exposing the site and applying the microparticles on or in close proximity to the site by painting, pipetting, spraying, injecting or the like. Microparticles can also be delivered to the site by endoscopy or by laparoscopy.

Poly(propylene fumarates) (PPF) are highly desirable biocompatible implantable carriers for use in repairing bone defects because they are an injectable, in situ polymerizable, biodegradable material. "Injectable" means that the material can be injected by syringe through a standard needle used for injecting pastes and gels. PPF, combined with a vinyl monomer (N-vinyl pyrrolidinone) and an initiator (benzoyl peroxide), forms an injectable solution that can be polymerized in situ. It is particularly suited for filling skeletal defects of a wide variety of sizes and shapes (see Suggs et al., *Macromolecules* 30.4318 (1997), Peter et al., *J. Biomater. Sci. Poly., Ed.* 10:363 (1999) and Yaszemski et al., *Tissue Eng.* 1:41 (1995), the entire teachings of which are incorporated herein by reference). The addition of solid phase components such as tricalcium phosphate and sodium chloride can improve the mechanical properties of PPF polymers (see Peter et al., *J. Biomed. Mater. Res.* 44:314 (1999), the entire teachings of which are incorporated herein by reference).

In yet another alternative, the pharmaceutical composition can be partially enclosed in a supporting physical structure such as a mesh, wire matrix, stainless steel cage, threaded interbody fusion cage and the like before administering to the site in need of bone growth.

Injectable delivery formulations may be administered intravenously or directly at the site in need of treatment. The injectable carrier may be a viscous solution or gel.

Delivery formulations include physiological saline, bacteriostatic saline (saline containing about 0.9% mg/mL benzyl alcohol), phosphate-buffered saline, Hank's solution, Ringer's-lactate, or liquids supplemented with albumin, methyl cellulose, or hyaluronic acid. Injectable matrices include polymers of poly(ethylene oxide) and copolymers of ethylene and propylene oxide (see Cao et al., *J. Biomater. Sci* 9.475 (1998) and Sims et al., *Plast Reconstr. Surg.* 98:843 (1996), the entire teachings of which are incorporated herein by reference).

Other compositions which are injectable matrices include the solutions of poly(propylene fumarate) copolymers described above and pastes of calcium phosphate ceramics (see Schmitz et al., *J. Oral Maxillofacial Surgery* 57:1122 (1999), the entire teachings of which are incorporated herein by reference). Injectable matrices can be injected directly to the site in need of bone growth and can conveniently be used to fill voids and fuse bones without the need for invasive surgery.

Methods for encapsulating compositions (such as in a coating of hard gelatin or cyclodextran) are known in the art (Baker, et al., "Controlled Release of Biological Active Agents," John Wiley and Sons, 1986).

Ointments are typically prepared using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in the desired concentration.

Creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, beegum, and the like. Upon formation of the emulsion, the active ingredients are added in the desired concentration.

Gels are comprised of a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent.

Diseases and conditions, treatable with thrombin peptide derivative dimers, for example, wounds and angioplasty, are often accompanied by symptoms and infirmities such as pain and infection. In certain instances it may be advantageous to co-administer one or more additional pharmacologically active agents along with a thrombin peptide derivative dimer to address such issues. For example, managing pain and inflamation, may require co-administration with analgesic or an anti-inflammatory agents. Managing infection may require co-administration with antimicrobial, antibiotic or disinfectant agents.

Thrombin peptide derivatives can be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc.* 88.2149 (1963); Meienhofer, Hormonal Proteins and Peptides, C. H. Li, Ed., Academic Press, 1983, pp. 48-267; and Barany and Merrifield, in *The Peptides*, E. Gross and J. Meienhofer, Eds., Academic Press, New York, 1980, pp. 3-285. Methods of solid phase peptide synthesis are described in Merrifield, R. B., *Science*, 232:341 (1986); Carpino, L. A. and Han, G. Y., *J. Org. Chem.*, 37: 3404 (1972); and Gauspohl, H. et al., *Synthesis*, 5:315 (1992)). The teachings of these six articles are incorporated herein by reference in their entirety.

Thrombin peptide derivative dimers can be prepared by oxidation of the monomer. Thrombin peptide derivative dimers can be prepared by reacting the thrombin peptide derivative with an excess of oxidizing agent. A well-known suitable oxidizing agent is iodine. Specific conditions are provided in Examples 1 and 2.

The invention is illustrated by the following examples which are not intended to be limiting in any way.

EXEMPLIFICATION

Example 1

Formation of Thrombin Peptide Dimer

TP508 was dissolved in a solution of a six parts acetic acid and one part water. A ten-fold molar excess of iodine was added and the reaction is allowed to proceed with stirring for 90 minutes at room temperature. Excess iodine was removed by extraction with $CCl_4$ (3 to 4 times). The dimerized peptide was purified by HPLC on a C18 reverse phase column to remove un-reacted monomers.

Example 2

TP508-Dimer

Conversion of TP508 to Dimer Over Time

TP508 was dissolved in saline (sterile 0.9% sodium chloride injectible solution) at 5 mg/mL and incubated at 4° C. Over a time period of 6 months, triplicate samples were taken at intervals from the solution. The samples were analyzed by HPLC to separate TP508-monomer, TP508-dimer and unknowns. The peak area of TP508-dimer, after three months, showed no decrease over time. No increase in the unknown peaks was observed. The results of FIG. 1 show that TP508-dimer does not revert to monomer over time.

The area percent of each HPLC peak was plotted in FIG. 1. The peak area percent corresponds directly to the percent of material in solution. The peak area of TP508-monomer decreased over time whereas the peak area of TP508-dimer increased over time. No increase in the unknown peaks were observed. The results of FIG. 1 show that TP508 converts to dimer over time.

TP508-DIMER Does Not Revert to Monomer Over Time

The peak area of TP508-dimer, after three months, showed no decrease over time. No increase in unknown peaks was observed. The results of FIG. 1 show that TP508-dimer does not revert to monomer over time.

Example 3

Wound Healing Activity of the Thrombin Peptide Dimer

Methodology and Study Design

The objective of this study was to evaluate the wound healing activity of the dimerized form of the thrombin peptide TP508. The study assessed the effect of the thrombin peptide dimer on wound closure.

Two, full-thickness, 2 cm-diameter excisions were created on the dorsum of male Sprague-Dawley rats. Both wounds on a given rat were together treated with either vehicle with a low-dose of thrombin peptide dimer, vehicle with a high-dose of thrombin peptide dimer, vehicle alone (negative control), or vehicle with TP508 (positive control), yielding a total of four treatment groups. Each group contained 6 rats. The activities of the high and low dose of thrombin peptide dimer were compared to vehicle alone and to TP508. Wound size was determined on post-wounding days 3, 7, and 10 by tracing the perimeter of the wound onto an acetate sheet and using digital analysis to compute the surface area of each wound.

Preparation of Treatment Solutions

Saline Solution

D-mannitol (20 mg) was dissolved in 12.5 mL of saline (sterile 0.9% sodium chloride injectible solution) to yield a solution of 8.9 mM D-mannitol in saline. This solution was used as the vehicle control for this experiment.

TP508 Solution

Lyophilized TP508 (1 mg) was dissolved in 1 mL of the D-mannitol/saline vehicle. The stock solution (1 mg/mL) was further diluted in vehicle to yield a working solution of 2.5 µg/ml. The working solution was maintained on ice throughout the experiment.

Thrombin Peptide Dimer Solution

High-Dose

TP508 (12.5 µg) and 2 mg D-mannitol were dissolved in 1.25 mL of saline (without D-mannitol) to yield a stock solution of 10 µg TP508 per mL of 8.9 mM D-mannitol in saline. The stock solution was used directly as the high treatment dose (0.4 µg per 40 µL per wound). The stock solution was maintained on ice throughout the experiment.

Low-Dose

The low treatment dose was prepared by further dilution of the stock dimer solution in the D-mannitol/saline vehicle to obtain a working solution of 2.5 µg per mL (0.1 µg per 40 µL per wound). The working solution was maintained on ice throughout the experiment.

Wound Treatment

Both wounds on a given animal received the same treatment: a single, topical application of a 40 µL volume containing vehicle alone, vehicle with TP508 (0.1 µg/mL), or vehicle with thrombin peptide dimer (0.1 µg/mL or 0.4 µg/mL).

Observations and Wound Size Analysis

The rats were observed for ten days following wounding, and no clinical signs of abnormal behavior, infection or toxicity were noted. On post-wounding days 3, 7, and 10, the wounds were evaluated by tracing the wound perimeter onto a flexible acetate sheet, then determining wound area with digital analysis software.

Figure 2:
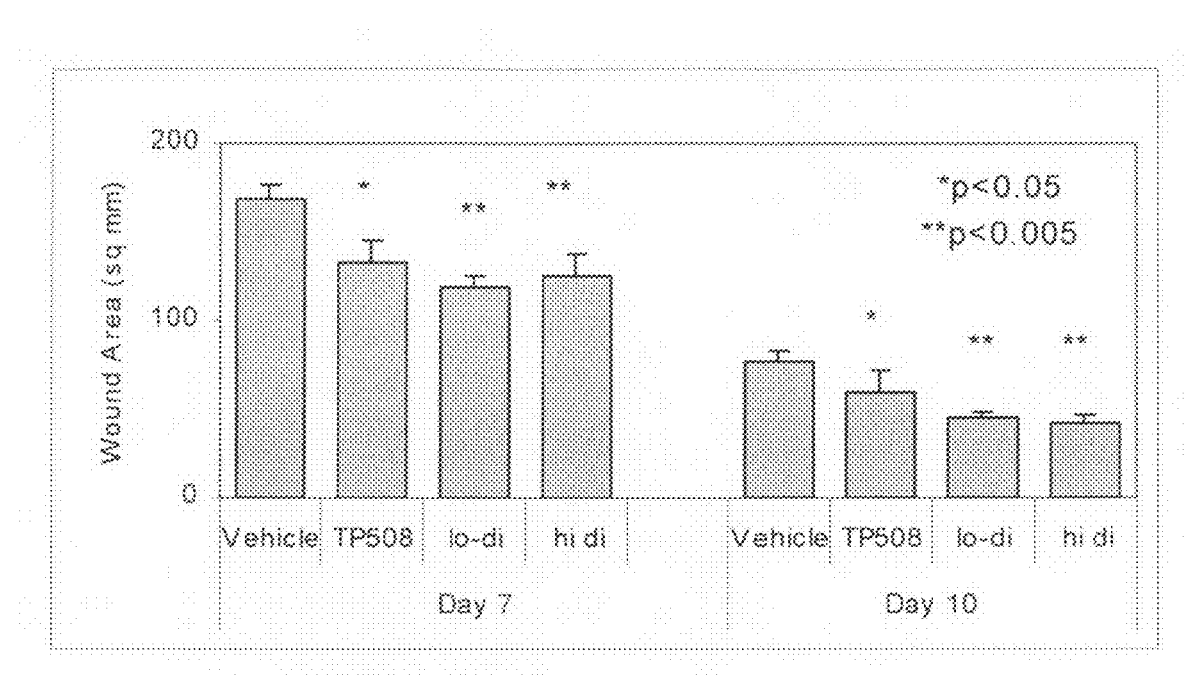
FIG. 2 is a graph showing that the thrombin peptide dimer retains the biological activity of TP508 with regard to the acceleration of wound healing. The graph shows wound area measurements (indicated in mm$^2$) on the dorsum of male Sprague-Dawley rats from post-wounding Day 7 and Day 10. The saline vehicle control is indicated as "vehicle," the TP508 control is indicated as "TP508," low-dose thrombin peptide dimer is indicated as "lo-di" and high-dose thrombin peptide dimer is indicated as "hi-di."

The results of the experiment are presented in FIG. 2. FIG. 2 shows wound area measurements from post-wounding Day 7 and Day 10. No differences in wound size between the groups were present on post-wounding Day 3. Each data point represents the mean and standard error of the mean of 12 wounds from 6 rats. Statistical comparisons between groups were made using a repeated measures analysis of variance; Fisher's LSD was used for post hoc testing between groups.

In this experiment, both TP508 and thrombin peptide dimer produced significantly smaller wounds than vehicle alone by post-wounding Day 7. TP508-treated wounds were 21.3% smaller in area than vehicle-controls, while wounds treated with the same dose of thrombin peptide dimer (0.1 µg per wound) were 29.2% smaller in area than vehicle-controls. The difference between TP508 and thrombin peptide dimer treatments was not statistically significant.

On day 10, as on Day 7, TP508 and both doses of thrombin peptide dimer generated wounds that were significantly smaller than those of the controls. In addition, a statistically significant difference was found on Day 10 between the TP508 treated group and the groups treated with the thrombin peptide dimer ($p<0.05$). On day 10, TP508 treated wounds were 23.1% smaller in area than vehicle-controls, while wounds treated with the same dose of thrombin peptide dimer (0.1 µg per wound) were 41.4% smaller in area than vehicle-controls.

In the low dose group, the thrombin peptide dimer was administered at an equivalent weight to the TP508 group. That is, each of these groups received 0.1 µg of peptide per wound, resulting in half as many moles of dimer as monomer administered to wounds in these two groups.

The results indicated that the thrombin peptide dimer is biologically active in accelerating wound closure. When viewed as "wound closure," the thrombin peptide dimer generated a statistically significant effect on healing that was equivalent to the effect of TP508.

While this invention has been particularly shown and described with references to preferred embodiments thereof, it will be understood by those skilled in the art that various changes in form and details may be made therein without departing from the scope of the invention encompassed by the appended claim.

What is claimed is:

1. A method of treating a subject in need of treatment with a thrombin receptor agonist, said method comprising administering to the subject an effective amount of a composition comprising a peptide dimer, said dimer comprising two thrombin peptide derivatives 12 to 23 amino acids in length, which, independently, comprise the amino acid sequence Asp-Ala-Cys-Glu-Gly-Asp-Ser-Gly-Gly-Pro-Phe-Val (SEQ ID NO:12); said thrombin peptide derivatives optionally comprising a C-terminal amide; and said thrombin peptide derivatives optionally comprising an acylated N-terminus, wherein the composition is greater than 95% free of monomer by weight.

2. The method of claim 1, wherein the thrombin peptide derivatives are the same.

3. The method of claim 1, wherein the thrombin peptide derivatives are covalently linked through a disulfide bond.

4. The method of claim 3, wherein the thrombin peptide derivatives do not comprise an N-terminal acyl group and optionally comprise a C-terminal amide represented by —C(O)NH$_2$.

5. The method of claim 4, wherein the thrombin peptide derivatives comprise the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:5), or a fragment thereof comprising SEQ ID NO:12.

6. The method of claim 4, wherein the thrombin peptide derivatives comprise the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:5).

7. The method of claim 4, wherein the thrombin peptide derivatives comprise the amino acid sequence Arg-Gly-Asp-Ala-Cys-Glu-Gly-Asp-Ser-Gly-Gly-Pro-Phe-Val (SEQ ID NO:2).

8. The method of claim 3, wherein the thrombin peptide derivatives comprise a C-terminal amide and optionally comprise an acylated N-terminus, wherein said C-terminal amide is represented by —C(O)NR$_b$R$_c$, wherein R$_b$ and R$_c$ are independently hydrogen, a C$_1$-C$_{10}$ substituted or unsubstituted aliphatic group, and said N-terminal acyl group is represented by R$_d$C(O)—, wherein R$_d$ is hydrogen, a C$_1$-C$_{10}$ substituted or unsubstituted aliphatic group.

9. A method of treating a subject in need of treatment with a thrombin receptor agonist, said method comprising administering to the subject an effective amount of a composition comprising two thrombin peptide derivatives 14 to 23 amino acids in length, which independently, comprise the amino acid sequence Arg-Gly-Asp-Ala-Cys-X$_1$-Gly-Asp-Ser-Gly-Gly-Pro-X$_2$-Val (SEQ ID NO:4), wherein X$_1$ is Glu or Gln and X$_2$ is Phe, Met, Leu, His or Val; wherein the thrombin peptide derivatives are the same and are covalently linked through a disulfide bond; and wherein the thrombin peptide derivatives do not comprise an N-terminal acyl group and optionally comprise a C-terminal amide represented by —C(O)NH$_2$; and wherein the composition is greater than 95% free of monomer by weight.

10. The method of claim 9, wherein the thrombin peptide derivatives have the amino acid sequence Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:6), wherein X$_1$ is Glu or Gln and X$_2$ is Phe, Met, Leu, His or Val; or wherein the thrombin peptide derivatives comprise SEQ ID NO:12.

11. The method of claim 9, wherein the thrombin peptide derivatives have the amino acid sequence Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:6), wherein X$_1$ is Glu or Gln and X$_2$ is Phe, Met, Leu, His or Val.

12. The method of claim 11, wherein X$_1$ is Glu and X$_2$ is Phe.

13. A method of treating a subject in need of treatment with a thrombin receptor agonist, said method comprising administering to the subject an effective amount of a composition comprising a peptide dimer comprising two thrombin peptide derivatives 14 to 23 amino acids in length, which, independently, comprise the amino acid sequence Arg-Gly-Asp-Ala-Cys-Glu-Gly-Asp-Ser-Gly-Gly-Pro-Phe-Val (SEQ ID NO:2), wherein said thrombin peptide derivatives optionally comprise a C-terminal amide; wherein said thrombin peptide derivatives optionally comprise an acylated N-terminus; and wherein the composition is greater than 95% free of monomer by weight.

14. The method of claim 13, wherein the thrombin peptide derivatives are covalently linked through a disulfide bond.

15. The method of claim 13, wherein the thrombin peptide derivatives comprise a C-terminal amide and optionally comprise an acylated N-terminus, and wherein said C-terminal amide is represented by —C(O)NRbRc, wherein R$_b$ and R$_c$ are independently hydrogen, a C$_1$-C$_{10}$ substituted or unsubstituted aliphatic group, or R$_b$ and R$_c$, taken together with the nitrogen to which they are bonded, form a non-aromatic heterocyclic group of up to 10 carbon atoms, and wherein said N-terminal acyl group is represented by R$_d$C(O)—, wherein R$_d$ is hydrogen or a C$_1$-C$_{10}$ substituted or unsubstituted aliphatic group.

16. The method of claim 13, wherein the thrombin peptide derivatives comprise an N-terminus which is unsubstituted and a C-terminus which is unsubstituted or which comprises an amide represented by —C(O)NH$_2$.

17. The method of claim 13, wherein the subject is in need of treatment to promote cardiac repair.

18. The method of claim 13, wherein the subject is in need of treatment to promote cartilage growth or repair.

19. The method of claim 13, wherein the subject is in need of bone growth.

20. The method of claim 13, wherein the subject is in need of a bone graft at a fracture site.

21. The method of claim 20, wherein the site is a segmental gap in a bone, a bone void or a non-union fracture.

22. The method of claim 13, wherein the subject is in need of treatment to promote wound healing.

23. The method of claim 13, wherein the subject is in need of treatment to inhibit restenosis.

24. The method of claim 13, wherein the thrombin peptide derivatives are the same.

25. A method of treating a subject in need of treatment with a thrombin receptor agonist, said method comprising administering to the subject an effective amount of a composition comprising a peptide dimer comprising two thrombin peptide derivatives 14 to 23 amino acids in length, which, independently, comprise the amino acid sequence Arg-Gly-Asp-Ala-Cys-X$_1$-Gly-Asp-Ser-Gly-Gly-Pro-X$_2$-Val (SEQ ID NO:4); wherein X$_1$, is Glu or Gln and X$_2$ is Phe, Met, Leu, His or Val; wherein said thrombin peptide derivatives optionally comprise a C-terminal amide; wherein said thrombin peptide derivatives optionally comprise an acylated N-terminus, and wherein the composition is greater than 95% free of monomer by weight.

26. The method of claim 25, wherein the thrombin peptide derivatives comprise Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:5).

27. The method of claim 25, wherein the thrombin peptide derivatives comprise Ala-Gly-Tyr-Lys-Pro-Asp-Glu-Gly- Lys-Arg-Gly-Asp-Ala-Cys-$X_1$-Gly-Asp-Ser-Gly-Gly-Pro-$X_2$-Val (SEQ ID NO:6), wherein $X_1$ is Glu or Gln and $X_2$ is Phe, Met, Leu, His or Val.

28. The method of claim 27, wherein $X_1$ is Glu and $X_2$ is Phe and the thrombin peptide derivatives comprise an N-terminus which is unsubstituted and a C-terminus which is unsubstituted or which comprises an amide represented by —C(O)NH$_2$.

29. A method of treating a subject in need of treatment with a thrombin receptor agonist, said method comprising administering to the subject an effective amount of a composition comprising a peptide dimer comprising two thrombin peptide derivatives, which, independently, comprise the polypeptide H-Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val-NH$_2$ (SEQ ID NO:11), wherein $X_1$ is Glu or Gln and $X_2$ is Phe, Met, Leu, His or Val and wherein the composition is greater than 95% free of monomer by weight.

30. The method of claim 29, wherein $X_1$ is Glu and $X_2$ is Phe.

31. A method of treating a subject in need of treatment with a thrombin receptor agonist, said method comprising administering to the subject an effective amount of a composition comprising a peptide dimer comprising two thrombin peptide derivatives 23 to 33 amino acids in length, which, independently, comprise the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:5); wherein the thrombin peptide derivatives are covalently linked by a disulfide bond, wherein said thrombin peptide derivatives optionally comprise a C-terminal amide, wherein said thrombin peptide derivatives optionally comprise an acylated N-terminus, and wherein the composition is greater than 95% free of monomer by weight.

32. A method of treating a subject in need of treatment with a thrombin receptor agonist, said method comprising administering an effective amount of a composition comprising a peptide dimer represented by the following structural formula:

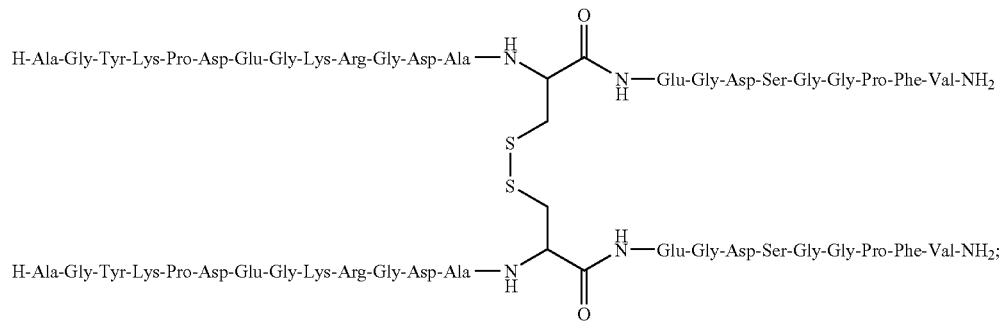

wherein the composition is greater than 95% free of monomer by weight.

* * * * *

UNITED STATES PATENT AND TRADEMARK OFFICE
CERTIFICATE OF CORRECTION

Page 1 of 1

PATENT NO. : 7,919,457 B2
APPLICATION NO. : 12/287703
DATED : April 5, 2011
INVENTOR(S) : Darrell H. Carney It is certified that error appears in the above-identified patent and that said Letters Patent is hereby corrected as shown below:

IN THE CLAIMS:

Column 22, Line 21, in claim 15: Delete "C(O)NRbRc" and replace with "C(O)NR$_b$R$_c$"

Signed and Sealed this
Twenty-eighth Day of August, 2012

David J. Kappos
*Director of the United States Patent and Trademark Office*